United States Patent [19]

Matusz

[11] Patent Number: 5,739,075
[45] Date of Patent: Apr. 14, 1998

[54] PROCESS FOR PREPARING ETHYLENE OXIDE CATALYSTS

[75] Inventor: Marek Matusz, Houston, Tex.

[73] Assignee: Shell Oil Company, Houston, Tex.

[21] Appl. No.: 540,233

[22] Filed: Oct. 6, 1995

[51] Int. Cl.$^6$ .............................. B01J 23/00; B01J 23/70
[52] U.S. Cl. .................... 502/302; 502/303; 502/304;
502/306; 502/317; 502/320; 502/322; 502/327;
502/328; 502/330; 502/332; 502/333; 502/334;
502/335; 502/336; 502/341; 502/346; 502/347;
502/348
[58] Field of Search .............................. 502/514, 302,
502/303, 304, 306, 317, 320, 322, 327,
328, 330, 332, 333, 334, 335, 336, 341,
346, 347, 348

[56] References Cited

U.S. PATENT DOCUMENTS

| 3,316,279 | 4/1967 | Fenton | 260/348.5 |
|---|---|---|---|
| 3,702,259 | 11/1972 | Nielsen | 117/37 R |
| 3,844,981 | 10/1974 | Cusumano | 252/471 |
| 3,962,136 | 6/1976 | Nielsen et al. | 252/454 |
| 3,962,285 | 6/1976 | Cusumano | 260/348.5 R |
| 3,972,829 | 8/1976 | Michalko | 252/430 |
| 4,005,049 | 1/1977 | Fields | 252/467 |
| 4,010,115 | 3/1977 | Nielsen et al. | 252/454 |
| 4,012,425 | 3/1977 | Nielsen et al. | 260/348.5 R |
| 4,212,772 | 7/1980 | Mross et al. | 252/476 |
| 4,272,443 | 6/1981 | Titzenthaler et al. | 260/348.34 |
| 4,278,562 | 7/1981 | Mross et al. | 252/430 |
| 4,324,699 | 4/1982 | Mross et al. | 252/463 |
| 4,356,312 | 10/1982 | Nielsen et al. | 549/534 |
| 4,444,899 | 4/1984 | Yamada et al. | 502/355 |
| 4,459,372 | 7/1984 | Arena | 502/351 |
| 4,532,231 | 7/1985 | Johnson | 502/347 |
| 4,536,482 | 8/1985 | Carcia | 502/177 |
| 4,548,921 | 10/1985 | Gues et al. | 502/330 |
| 4,711,873 | 12/1987 | Suzukamo et al. | 502/344 |
| 4,742,034 | 5/1988 | Boxhoorn et al. | 502/231 |
| 4,761,394 | 8/1988 | Lauritzen | 502/348 |
| 4,766,105 | 8/1988 | Lauritzen | 502/216 |
| 4,786,626 | 11/1988 | Suzukamo et al. | 502/344 |
| 4,808,738 | 2/1989 | Lauritzen | 549/536 |
| 4,837,194 | 6/1989 | Hayden | 502/348 |
| 4,874,739 | 10/1989 | Boxhoorn | 502/218 |
| 4,897,498 | 1/1990 | Monnier et al. | 549/534 |
| 4,908,343 | 3/1990 | Bhasin | 502/218 |
| 4,992,409 | 2/1991 | Michaels et al. | 502/341 |
| 5,011,809 | 4/1991 | Herzog | 502/348 |
| 5,028,577 | 7/1991 | Michaels et al. | 502/243 |
| 5,037,794 | 8/1991 | Magistro | 502/355 |
| 5,055,442 | 10/1991 | Osaka et al. | 502/439 |
| 5,057,481 | 10/1991 | Bhasin | 502/208 |
| 5,063,195 | 11/1991 | Jin et al. | 502/348 |
| 5,071,815 | 12/1991 | Wallace et al. | 502/302 |
| 5,072,886 | 12/1991 | Morrison et al. | 241/1 |
| 5,081,096 | 1/1992 | Monnier et al. | 502/348 |
| 5,081,324 | 1/1992 | Michaels et al. | 585/500 |
| 5,100,859 | 3/1992 | Gerdes et al. | 502/439 |
| 5,102,848 | 4/1992 | Soo et al. | 502/218 |
| 5,130,286 | 7/1992 | Michaels et al. | 502/341 |
| 5,153,165 | 10/1992 | Lowery et al. | 502/341 |
| 5,364,826 | 11/1994 | Kemp | 502/315 |
| 5,380,697 | 1/1995 | Matusz et al. | 502/348 |
| 5,447,897 | 9/1995 | Kemp | 502/303 |

FOREIGN PATENT DOCUMENTS

| 199396 | 10/1986 | European Pat. Off. | B01J 21/04 |
|---|---|---|---|
| 327356 | 6/1989 | European Pat. Off. | C07D 301/10 |
| 501317 | 3/1991 | European Pat. Off. | B01J 23/66 |
| 56108533 | 1/1980 | Japan | B01J 23/66 |
| 4363139-A | 6/1991 | Japan | B01J 23/50 |
| 1325715 | 8/1973 | United Kingdom | C07D 1/14 |

Primary Examiner—Walter D. Griffin
Assistant Examiner—In Suk Bullock
Attorney, Agent, or Firm—Pamela J. McCollough

[57] ABSTRACT

This invention relates to a process for the preparation of a catalyst suitable for the production of ethylene oxide which process comprises depositing a promoting amount of a salt of a rare earth metal and a promoting amount of a salt of an alkaline earth metal and/or a salt of a Group VIII transition metal on a porous, refractory support, calcining the support, and thereafter depositing a catalytically effective amount of silver, a promoting amount of alkali metal, and optionally, a promoting amount of rhenium and/or a promoting amount of a rhenium co-promoter selected from sulfur, molybdenum, tungsten, chromium, phosphorus, boron and mixtures thereof, on the support, and subsequently drying the support.

52 Claims, 1 Drawing Sheet

FIG. 1

PROCESS FOR PREPARING ETHYLENE OXIDE CATALYSTS

FIELD OF THE INVENTION

The invention relates to a process for the preparation of silver-containing catalysts suitable for the preparation of ethylene oxide and to the use of the catalyst for the preparation of ethylene oxide.

BACKGROUND OF THE INVENTION

Catalysts for the production of ethylene oxide from ethylene and molecular oxygen are generally supported silver catalysts. Such catalysts are typically promoted with alkali metals. The use of small amounts of the alkali metals potassium, rubidium and cesium were noted as useful promoters in supported silver catalysts in U.S. Pat. No. 3,962, 136, issued Jun. 8, 1976, and U.S. Pat. No. 4,010,115, issued Mar. 1, 1977. The use of other co-promoters, such as rhenium, or rhenium along with sulfur, molybdenum, tungsten and chromium is disclosed in U.S. Pat. No. 4,766,105, issued Aug. 23, 1988, and U.S. Pat. No. 4,808,738, issued Feb. 28, 1989. U.S. Pat. No. 4,908,343, issued Mar. 13, 1990, discloses a supported silver catalyst containing a mixture of a cesium salt and one or more alkali metal and alkaline earth metal salts.

U.S. Pat. No. 3,844,981 issued Oct. 29, 1974, U.S. Pat. No. 3,962,285 issued Jun. 8, 1976 and British Patent No. 1,325,715, published Aug. 8, 1973, disclose the use of silver-rhenium ethylene oxide catalysts. In these patents a high surface area silver derivative such as silver oxide is impregnated with a rhenium solution and subsequently reduced to provide metallic rhenium alloyed with the silver. The '285 patent discloses the use of KOH to precipitate $Ag_2O$ from $AgNO_3$. There is no disclosure in the patents of the use of suitable inert supports such as porous refractory supports. U.S. Pat. No. 4,548,921, issued Oct. 22, 1985, discloses the use of rhenium in silver-supported ethylene oxide catalysts. In this reference, the rhenium is first placed on the support in the form of finely divided metal particles and the silver is subsequently deposited on the outer surface of the particles. U.S. Pat. No. 3,316,279, issued Apr. 25, 1967, discloses the use of rhenium compounds, particularly ammonium and alkali metal perrhenates for the oxidation of olefins to olefin oxides. In this reference, however, the rhenium compounds are used, unsupported, along with a reaction modifier (cyanides, pyridines or quinolines) in a liquid phase reaction. U.S. Pat. No. 3,972,829, issued Aug. 3, 1976, discloses a method for distributing catalytically active metallic components on supports using an impregnating solution of catalyst precursor compound and an organic thioacid or a mercaptocarboxylic acid. Catalytically active metals include metals of Groups IVA, IB, VIB, VIIB and VIII, including rhenium and which may be in either the oxidized or reduced state. U.S. Pat. No. 4,459,372, issued Jul. 10, 1984, discloses the use of rhenium metal in combination with a surface metallated (using Ti, Zr, Hf, V, Sb, Pb, Ta, Nb, Ge and/or Si) alumina or silica. U.S. Pat. No. 4,005,049, issued Jan. 25, 1977, teaches the preparation of a silver/transition metal catalyst useful in oxidation reactions. In this instance, the silver serves as both a catalyst and a support for the transition metal co-catalyst. In U.S. Pat. No. 4,536,482, issued Aug. 20, 1985, catalytically active metals such as Ag and Re are co-sputtered along with a co-sputtered support material on a particular support. U.S. Pat. No. 4,257,967, issued Mar. 24, 1981, discloses a catalyst combination of reduced silver, a carbonate of a rare earth metal and yttrium, a salt of an alkali or alkaline earth metal and a catalyst carrier. None of these references disclose pre-doping a catalyst support with a promoting amount of a salt of a rare earth metal and a promoting amount of a salt of an element selected from the group consisting of an alkaline earth metal, a Group VIII transition metal and mixtures thereof, prior to the addition of silver and alkali metal.

SUMMARY OF THE INVENTION

The invention relates to a process for the preparation of a catalyst suitable for the production of ethylene oxide from ethylene and molecular oxygen in the vapor phase which process comprises depositing a promoting amount of a salt of a rare earth metal and a promoting amount of a salt of an element selected from the group consisting of an alkaline earth metal, a Group VIII transition metal and mixtures thereof, on a porous, refractory support, calcining the support, and thereafter depositing a catalytically effective amount of silver, a promoting amount of alkali metal, and optionally, a promoting amount of rhenium and/or a promoting amount of a rhenium co-promoter selected from sulfur, molybdenum, tungsten, chromium, phosphorus, boron and mixtures thereof, on the support, and subsequently drying the catalyst.

It has been found that catalysts pre-doped, pretreated or pre-impregnated with a promoting amount of a salt of a rare earth metal and a promoting amount of a salt of an element selected from the group consisting of an alkaline earth metal, a Group VIII transition metal and mixtures thereof, have improved selectivity stabilities when compared with those obtained with catalysts which have not been pre-doped with a rare earth and an alkaline earth metal and/or a Group VIII transition metal.

DESCRIPTION OF THE PREFERRED EMBODIMENTS

Generally, in the vapor phase reaction of ethylene with oxygen to produce ethylene oxide, the ethylene is present in at least a double amount (on a molar basis) compared with oxygen, but frequently is often much higher. Therefore, the conversion is calculated according to the mole percentage of oxygen which has been consumed in the reaction to form ethylene oxide and any oxygenated by-products. The oxygen conversion is dependent on the reaction temperature, and the reaction temperature is a measure of the activity of the catalyst employed. The value $T_{40}$ indicates the temperature at 40 mole percent oxygen conversion in the reactor and the value $T_{40}$ is expressed in °C. This temperature for any given catalyst is higher when the conversion of oxygen is higher. The selectivity (to ethylene oxide) indicates the molar amount of ethylene oxide in the reaction product compared with the total molar amount of ethylene converted. In this specification, the selectivity is indicated as $S_{40}$, which means the selectivity at 40 mole percent oxygen conversion. The selectivity of silver-based ethylene oxide catalysts can and will decrease over a period of time of usage. Therefore, from an economical and practical standpoint, it is not only the initial selectivity of a catalyst which is important, but also the rate at which the selectivity declines. In fact, significant improvement in lowering the decline rate of a catalyst can prove more economically attractive than a high initial selectivity. Thus, the rate at which a catalyst loses selectivity is a predominant factor influencing the efficiency of any particular catalyst, and lowering this decline rate can lead to significant savings in terms of minimizing waste of the ethylene starting material.

The catalysts of the instant invention comprise a catalytically effective amount of silver, a promoting amount of alkali metal, and optionally, a promoting amount of rhenium and/or a promoting amount of a rhenium co-promoter selected from sulfur, chromium, molybdenum, tungsten and mixtures thereof, supported on a porous, refractory support which has been pretreated with a promoting amount of a salt of a rare earth metal and a promoting amount of a salt of an element selected from the group consisting of an alkaline earth metal, a Group VIII transition metal and mixtures thereof.

In general, the catalysts of the present invention are prepared by impregnating porous refractory supports with rare earth compound(s), complex(es) and/or salt(s) and at least one of alkaline earth metal compound(s), complex(es) and/or salt(s) and Group VIII transition metal compound(s), complex(es) and/or salt(s) dissolved in a suitable solvent sufficient to cause deposition on the support of from about 0.05 percent by weight to about 10 percent by weight of the total catalyst, preferably from about 0.05 by weight to about 2 percent by weight of the total catalyst, of rare earth, and from about 0.01 percent by weight to about 5 percent by weight of the total catalyst, preferably from about 0.02 percent by weight to about 3 percent by weight of the total catalyst, of alkaline earth metal and/or Group VIII transition metal. The porous refractory support is then calcined and thereafter impregnated with silver ions or compound(s), complex(es) and/or salt(s) dissolved in a suitable solvent sufficient to cause deposition on the support of from. about 1 to about 40 percent by weight, preferably from about 1 to about 25 percent by weight, basis the weight of the total catalyst, of silver. The impregnated support is subsequently separated from the solution and the deposited silver compound is reduced to metallic silver. Also deposited on the support either prior to, coincidentally with, or subsequent to the deposition of the silver will be suitable ions, or compound(s) and/or salt(s) of alkali metal dissolved in a suitable solvent. Optionally deposited on the support either prior to, coincidentally with, or subsequent to the deposition of the silver and/or alkali metal will be suitable rhenium ions or compound(s), complex(es) and/or salt(s) dissolved in an appropriate solvent, and/or suitable ions or salt(s), complex (es) and/or compound(s) of sulfur, molybdenum, tungsten, phosphorus, boron and/or chromium dissolved in an appropriate solvent. In the present invention, the rare earth compound(s), complex(es) and/or salt(s) dissolved in an appropriate solvent and the alkaline earth and/or transition metal compound(s), complex(es) and/or salt(s) dissolved in an appropriate solvent will be deposited on the carrier prior to the deposition of the silver, alkali metal, rhenium, if present, and rhenium co-promoter, if present.

The carrier or support employed in these catalysts in its broadest aspects can be any of the large number of conventional, porous refractory catalyst carriers or support materials which are considered relatively inert in the presence of ethylene oxidation feeds, products and reaction conditions. Such conventional materials are known to those skilled in the art and may be of natural or synthetic origin and preferably are of a macroporous structure, i.e., a structure having a surface area below about 10 m$^2$/g and preferably below about 3 m$^2$/g. Particularly suitable supports are those of aluminous composition. Examples of supports which have been used as supports for different catalysts and which could, it is believed, be used as supports for ethylene oxide catalysts are the aluminum oxides (including the materials sold under the trade name "Alundum"), charcoal, pumice, magnesia, zirconia, kieselguhr, fuller's earth, silicon carbide, porous agglomerates comprising silica and/or silicon carbide, silica, magnesia, selected clays, artificial and natural zeolites and ceramics. Refractory supports especially useful in the preparation of catalysts in accordance with this invention comprise the aluminous materials, in particular those comprising alpha alumina. In the case of alpha alumina-containing supports, preference is given to those having a specific surface area as measured by the B.E.T. method of from about 0.03 m$^2$/g to about 10 m$^2$/g, preferably from about 0.05 m$^2$/g to about 5 m$^2$/g, more preferably from about 0.1 m$^2$/g to about 3 m$^2$/g, and a water pore volume as measured by conventional water absorption techniques of from about 0.1 to about 0.75 cc/g by volume. The B.E.T. method for determining specific surface area is described in detail in Brunauer, S., Emmet, P. Y. and Teller, E., *J. Am. Chem. Soc.*, 60, 309–16 (1938).

Certain types of alpha alumina containing supports are particularly preferred. These alpha alumina supports have relatively uniform pore diameters and are more fully characterized by having B.E.T. specific surface areas of from about 0.1 m$^2$/g to about 3 m$^2$/g, preferably from about 0.1 m$^2$/g to about 2 m$^2$/g, and water pore volumes of from about 0.10 cc/g to about 0.55 cc/g. Typical properties of some supports found particularly useful in the present invention are presented in Table I. Suitable manufacturers of carriers comparable to those in Table I include Norton Company and United Catalysts, Inc. (UCI).

TABLE I

|  | Carrier | | | | | |
|---|---|---|---|---|---|---|
|  | A | B | C | D | E | F |
| B.E.T. Surface Area, m$^2$/g[a] | 0.21 | 0.42 | 0.51 | 0.48 | 0.68 | 2.06 |
| Water Pore Volume, cc/g | 0.26 | 0.36 | 0.38 | 0.49 | 0.37 | 0.65 |
| Crush Strength, FPCS, lbs[b] | 20 | 15 | 21 | 14 | 28 | No Data |
| Total Pore Volume, Hg, cc/g[c] | 1.26 | 0.42 | 0.40 | 0.46 | 0.40 | 0.65 |
| Average Pore Diameter, Hg, Å[c] | 620 | 560 | — | 550 | — | 1000 |
| Median Pore Diameter, Hg, microns[c,d] | 3.7 | 2.7 | 3.5 | 3.4 | 1.7 | 2.5 |
| Percent Pore Volume in Pores | 90.0% | 88.5% | 93.0% | 89.1% | — | 94.1% |

TABLE I-continued

|  | Carrier | | | | | |
|---|---|---|---|---|---|---|
|  | A | B | C | D | E | F |
| Greater Than 350Å[c] Percent Pore Volume in Pores Greater Than 1 Micron[c] | 87.0% | 82.5% | 77.0% | 82.3% | — | 61.0% |
| % Wt. Alpha Alumina | 99.5 | 98 | 98.8 | 98.5 | >98 | 70–75 |
| Water Leachable Na, ppmw | 12 | 53 | 69 | 24 | 18 | No Data |
| Acid-Leachable Na, ppmw | 40 | 96 | 188 | 51 | 172 | No Data |
| Water Leachable K, ppmw | 5 | 22 | 32 | 22 | 119 | No Data |
| Acid-Leachable Fe, ppmw | 2 | 5 | — | 1 | — | No Data |
| % Wt. SiO$_2$ | .5 | 2 | 0.1 | 15 | 0.17 | 25–30 |

[a]Method of Brunauer, Emmet and Teller, loc. cit.
[b]Flat Plate Crush Strength, single pellet.
[c]Determined by mercury intrusion to 55,000 psia using Micrometrics Autopore 9200 or 9210 (130° Contact angle, 0.473 N/m surface tension of Hg).
[d]Median pore diameter represents the pore diameter wherein 50% of the total pore volume is found in pores having less than (or greater than) the median pore diameter.

Of the carriers listed in TABLE I, C is preferred because it provides catalysts which have high initial selectivities.

The support, irrespective of the character of the support or carrier used, is preferably shaped into particles, chunks, pieces, pellets, rings, spheres, wagon wheels, and the like of a size suitable for use in fixed bed reactors. Conventional commercial fixed bed reactors are typically in the form of a plurality of parallel elongated tubes (in a suitable shell) approximately 0.7 to 2.7 inches O.D. and 0.5 to 2.5 inches I.D. and 15–45 feet long filled with catalyst. In such reactors, it is desirable to use a support formed into a rounded shape, such as, for example, spheres, pellets, rings, tablets and the like, having diameters from about 0.1 inch to about 0.8 inch.

Particular supports having differing properties such as surface area and pore volume may be selected in order to provide particular catalytic properties. With regard to surface area (B.E.T.), a possible lower limit is about 0.01 m$^2$/g and a possible upper limit is about 10 m$^2$/g. With regard to water pore volume, a possible lower limit is about 0.05 cc/g and a possible upper limit is about 0.8 cc/g.

The catalysts of the present invention are prepared by a technique in which a rare earth promoter in the form of soluble salts and/or compounds and an alkaline earth metal promoter in the form of soluble salts and/or compounds and/or a Group VIII transition metal promoter in the form of soluble salts and/or compounds are deposited on the support which is then subjected to partial drying or to a thermal treatment sufficient to allow deposition of the rare earth salts and the alkaline earth metal and/or Group VIII transition metal salts, and, while not wishing to be bound by any particular theory, presumed complexation with the anionic components on the surface of the catalyst. Thereafter, the alkali metal promoter(s), the rhenium promoter, if present, and the rhenium co-promoter, if present, in the form of soluble salts and/or compounds are deposited on the catalyst and/or support prior to, simultaneously with, or subsequent to the deposition of the silver and each other. The alkali metals may be deposited at one step of the process and the rhenium, if present, and/or the rhenium co-promoter, if present, at a different step or steps. The preferred method is to deposit silver, alkali metal, rhenium and rhenium co-promoter simultaneously on the support, that is, in a single impregnation step, although it is believed that the individual or concurrent deposition of the alkali metal, rhenium, if present, and rhenium co-promoter, if present, prior to and/or subsequent to the deposition of the silver would also produce suitable catalysts. The rare earth promoter and the alkaline earth and/or Group VIII transition metal promoters, however must be deposited on the support prior to all of the other catalyst components and the support must then be calcined to a degree sufficient to fix the rare earth and the alkaline earth and/or Group VIII transition promoters on the support before deposition of the other catalyst components. The pre-impregnation or pre-doping of the catalyst with a promoting amount of rare earth in combination with a promoting amount of an alkaline earth metal and/or Group VIII transition metal results in a catalyst having improved selectivity stability.

Promoting amounts of rare earth promoter ions, salt(s), compound(s) and/or complex(es) are impregnated onto the carrier along with promoting amounts of alkaline earth metal ions, salt(s), compound(s) and/or complex(es), and/or Group VIII transition metal ions, salt(s), compound(s) and/or complex(es) are impregnated onto the carrier, and the carrier is calcined to a degree sufficient to fix the rare earth promoter and the alkaline earth metal and/or Group VIII transition metal promoter to the support prior to impregnation with silver, alkali metal rhenium, if present, and rhenium co-promoter, if present. It is necessary for purposes of this invention that the rare earth promoter and the alkaline earth metal and/or Group VIII transition metal promoter be added before the other components, i.e. the silver, alkali metal, rhenium, if present, and rhenium co-promoter, if present, are impregnated or deposited on the support and that, following the deposition of the rare earth and the alkaline earth metal and/or the Group VIII transition metal, the impregnated support is calcined to an extent sufficient to allow deposition and fixing of the rare earth and the alkaline earth metal and/or the Group VIII transition metal to the support. Although rare earth metals, alkaline earth metals and Group VIII transition metals exist in a pure metallic state, they are not suitable for use in that form. They are used as ions or compounds of rare earth metals, ions or compounds of alkaline earth metals and/or ions or compounds of Group VIII transition metals dissolved in a suitable solvent for impregnation purposes. The carrier is pre-impregnated or pre-doped with a solution of rare earth promoter ions, salt(s) and/or compound(s) and either a solution of alkaline earth metal ions, salt(s) and/or compound(s) or a solution of Group VII transition metal ions, salt(s) and/or compound(s), or a mixture thereof, prior to the impregnation of the silver ions or salt(s), complex(es), and/or compound(s) and the other promoters, i.s., alkali metal, optionally, rhenium, and optionally, rhenium co-promoter. As used herein, the terms "pre-doping", "pre-impregnation", "pretreating" and similar terms are all used interchangeably to refer to the addition of a rare earth promoter and a promoter selected from the group consisting of an alkaline earth metal promoter, a Group VIII transition metal promoter and mixtures thereof, to a catalyst or support which is partially dried prior to the deposition or impregnation of the catalyst or carrier with silver, alkali metal, rhenium, if any, and rhenium co-promoter, if any.

The promoting amount of rare earth utilized to predope the catalyst carrier will depend on several variables, such as, for example, the surface area and pore structure and surface chemical properties of the carrier used. The amount of rare earth promoter deposited upon the support or present on the catalyst generally lies between about 0.05 percent by weight to about 10 percent by weight of the total catalyst, preferably from about 0.05 by weight to about 2 percent by weight of the total catalyst. The promoting effect provided by the rare earth will vary depending upon particular properties and characteristics, such as, for example, reaction conditions, catalyst preparative techniques, surface area and pore structure and surface chemical properties of the carrier utilized, the silver, alkali metal, rhenium and rhenium co-promoter content of the catalyst, and other compounds, cations or anions present in addition to those containing the alkali metal, rhenium and rhenium co-promoter, if present, or compounds remaining from the impregnating solution, and the above-defined limits were selected to cover the widest possible variations in properties and characteristics. The effects of these variations in properties are readily determined by experimentation. Without intending to limit the scope of the invention, it is believed that the rare earth promoter or promoters are present on the catalyst in the form of oxides or oxygen-bound species, or surface compounds or surface complexes rather than as metals, although for purposes of convenience in this specification and claims, they are referred to as "rare earth(s)", "rare earth metal(s)", "rare earth metal compound(s)", "rare earth compound(s)", and/or "rare earth promoters" even though they are not present on the catalyst as metals. For purposes of convenience, the amount of rare earth deposited on the support or present on the catalyst is expressed as the metal rather than in the cationic or compounds or complexes or surface compounds or surface complexes. More particularly, it is believed that the rare earth metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

As used herein, the terms "rare earth metal" and "rare earth" and "lanthanide" refer to the rare earth metals or elements having atomic numbers 57 (lanthanum) through 71 (lutecium) in the Periodic Table of the Elements i.e., lanthanum, cerium, praseodymium, neodymium, promethium, samarium, europium, gadolinium, terbium, dysprosium, holmium, erbium, thulium, yttererbium, thulium, ytterbium, and lutetium. As used herein, the term "mixtures of rare earth metals" refers to the use of two or more of the rare earth metals having atomic numbers 57 through 71 in the Periodic Table of the Elements, as appropriate, to provide a promoting effect.

In a preferred embodiment, the rare earth metal is selected from the group consisting of lanthanum, cerium, neodymium, samarium, gadolinium, dysprosium, erbium, ytterbium, and mixtures thereof, with lanthanum, cerium, neodymium, gadolinium, ytterbium, and mixtures thereof being particularly preferred. It should be understood that the use of Markush terminology in this specification and claims to indicate the rare earth metals cerium and/or neodymium and/or samarium and/or gadolinium and/or dysprosium and/or erbium and/or ytterbium is not meant and does not exclude the presence, inclusion or the use of the remainder of the rare earth metals having atomic numbers 57 through 71 in the Periodic Table of the Elements. Thus, the use of a Markush recitation in the instant specification and claim means that the elements in the recitation are included, but others are not excluded, i.e., the Markush recitation is an open-ended recitation.

When a promoting amount of an alkaline earth metal is used along with a rare earth to pre-dope the catalyst carrier, the amount of alkaline earth metal utilized to pre-dope the catalyst carrier will depend on several variables, such as, for example, the surface area and pore structure and surface chemical properties of the carrier used. The amount of alkaline earth metal promoter deposited upon the support or present on the catalyst generally lies between about 0.01 percent by weight to about 5 percent by weight of the total catalyst, preferably from about 0.02 percent by weight to about 3 percent by weight of the total catalyst. Most preferably, the amount ranges between about 0.02 percent by weight and about 2 percent by weight of the total catalyst. The promoting effect provided by the alkaline earth metal will vary depending upon particular properties and characteristics, such as, for example, reaction conditions, catalyst preparative techniques, surface area and pore structure and surface chemical properties of the carrier utilized, the silver, alkali metal, rhenium and rhenium co-promoter content of the catalyst, and other compounds, cations or anions present in addition to those containing the alkali metal, rhenium and rhenium co-promoter, if present, or compounds remaining from the impregnating solution, and the above-defined limits were selected to cover the widest possible variations in properties and characteristics. The effect, of these variations in properties are readily determined by experimentation. The alkaline earth metal promoter or promoters are presumably present on the catalyst in the form of oxides or oxygen-bound species, or surface compounds or surface complexes rather than as metals, although for purposes of convenience in this specification and claims, they are referred to as "alkaline earth metal", "alkaline earth metal compound(s)", and/or "alkaline earth metal promoter(s)" even though they are not present on the catalyst as metals. For purposes of convenience, the amount of alkaline earth metal deposited on the support or present on the catalyst is expressed as the element rather than in the cationic or compounds or complexes or surface compounds or surface complexes. Without intending to limit the scope of the invention, it is believed that the alkaline earth metal compounds are oxidic compounds. More particularly, it is believed that the alkaline earth metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

As used herein, the term "mixtures of alkaline earth metal compounds" refers to the use of two or more compounds of alkaline earth metals, as appropriate, to provide a promoting effect. In a preferred embodiment, the alkaline earth metal is selected from the group consisting of magnesium, calcium, strontium, barium and mixtures thereof, with magnesium, calcium and mixtures thereof being particularly preferred.

When a promoting amount of a Group VIII transition metal is used along with a rare earth to pre-dope the catalyst carrier, the amount of Group VIII transition metal utilized to pre-dope the catalyst carrier will depend on several variables, such as, for example, the surface area and pore structure and surface chemical properties of the carrier used. The amount of Group VIII transition metal promoter deposited upon the support or present on the catalyst generally lies between about 0.01 percent by weight to about 5 percent by weight of the total catalyst, preferably from about 0.02 percent by weight to about 3 percent by weight of the total catalyst. Most preferably, the amount ranges between about 0.02 percent by weight and about 2 percent by weight of the total catalyst. The promoting effect provided by the Group VIII transition metal will vary depending upon particular properties and characteristics, such as, for example, reaction conditions, catalyst preparative techniques, surface area and pore structure and surface chemical properties of the carrier utilized, the silver, alkali metal, rhenium and rhenium co-promoter content of the catalyst, and other compounds, cations or anions present in addition to those containing the alkali metal, rhenium and rhenium co-promoter, if present, or compounds remaining from the impregnating solution, and the above-defined limits were selected to cover the widest possible variations in properties and characteristics. The effect, of these variations in properties are readily determined by experimentation. The Group VIII transition metal promoter or promoters are presumably present on the catalyst in the form of oxides or oxygen-bound species, or surface compounds or surface complexes rather than as metals, although for purposes of convenience in this specification and claims, they are referred to as "Group VIII transition metal", "Group VIII transition metal compound (s)", and/or "Group VIII transition metal promoter(s)" even though they are not present on the catalyst as metals. For purposes of convenience, the amount of Group VIII transition metal deposited on the support or present on the catalyst is expressed as the element rather than in the cationic or compounds or complexes or surface compounds or surface complexes. Without intending to limit the scope of the invention, it is believed that the Group VIII transition metal compounds are oxidic compounds. More particularly, it is believed that the Group VIII transition metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

As used herein, the term "mixtures of Group VIII transition metal compounds" refers to the use of two or more compounds of Group VIII transition metals, as appropriate, to provide a promoting effect. In a preferred embodiment, the Group VIII transition metal is selected from the group consisting of cobalt, iron, nickel, ruthenium, rhodium, palladium and mixtures thereof.

The promoting effect provided by the rare earth and alkaline earth metal and/or Group VIII transition metal pre-dopants can be affected by a number of variables such as for example, reaction conditions, catalyst preparative techniques, surface area and pore structure and surface chemical properties of the support, the silver, alkali metal, rhenium, if present, and, if present, rhenium co-promoter content of the catalyst, and the presence of other cations and anions present on the catalyst alone or in combination with the alkali metal and/or rhenium and/or rhenium co-promoter and/or rare earth and alkaline earth metal and/or Group VIII transition metal. The presence of other activators, stabilizers, promoters, enhancers or other catalyst improvers can also affect the promoting effects of the rare earth and alkaline earth metal and/or Group VIII transition metal. It is understood that any supported silver-based, alkali metal promoted ethylene oxide catalyst which contains other cations and/or anions or any other activators, promoters, enhancers, stabilizers or the catalyst improvers and which contains a pre-doped amount of rare earth in combination with alkaline earth metal and/or Group VIII transition metal which provides a promoting effect, more preferably which provides improved selectivity stabilities when compared to those obtained under the same reaction conditions with the same catalyst which contains no pre-doped rare earth and alkaline earth metal and/or Group VIII transition metal promoters, will fall within the scope of the instant invention and claims.

Promoting amounts of alkali metal or mixtures of alkali metal are deposited on a porous support which has been pretreated with a promoting amount of a salt of a rare earth metal and a salt of an element selected from the group consisting of an alkaline earth metal, a Group VIII transition metal and mixtures thereof, by impregnation using a suitable solution. Although alkali metals exist in a pure metallic state, they are not suitable for use in that form. They are used as ions or compounds of alkali metals dissolved in a suitable solvent for impregnation purposes. The carrier is impregnated with a solution of alkali metal promoter ions, salt(s) and/or compound(s) before, during or after impregnation of the silver ions or salt(s), complex(es), and/or compound(s) has taken place. An alkali metal promoter may even be deposited on the carrier after reduction to metallic silver has taken place. The promoting amount of alkali metal utilized will depend on several variables, such as, for example, the surface area and pore structure and surface chemical properties of the carrier used, the silver content of the catalyst and the particular ions used in conjunction with the alkali metal cation, rare earth, alkaline earth metal and/or Group VIII transition metal, rhenium, if present, and rhenium co-promoter, if present, and the amounts of cesium, rhenium, if any, and rhenium co-promoter, if any, present. The amount of alkali metal promoter deposited upon the support or present on the catalyst generally lies between about 10 parts per million and about 3000 parts per million, preferably between about 15 parts per million and about 2000 parts per million and more preferably, between about 20 parts per million and about 1500 parts per million by weight of total catalyst. Most preferably, the amount ranges between about 50 parts per million and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, and other compounds, cations or anions present in addition to alkali metal ions such as ions added with the alkali metal, rare earth, alkaline earth metal and/or Group VIII transition metal, rhenium, if present, and rhenium co-promoter, if present, or compounds remaining from the impregnating solution, and the above-defined limits were selected to cover the widest possible variations in properties and characteristics. The effects of these variations in properties are readily determined by experimentation. The alkali metal promoters are present on the catalysts in the form of cations (ions) or compounds of complexes or surface compounds or surface complexes rather than as the extremely active free alkali metals, although for convenience purposes in this specification and claims they are referred to as "alkali metal" or "alkali metal promoters" even though they are not present on the catalyst as metallic elements. For purposes of convenience, the amount of alkali metal deposited on the support or present on the catalyst is expressed as the metal. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

In a preferred embodiment, at least a major proportion (greater than 50%) of the alkali metals comprise the higher alkali metals. As used herein, the term "higher alkali metal" and cognates thereof refers to the alkali metals selected from the group consisting of potassium, rubidium, cesium and mixtures thereof. As used herein, the term "alkali metal" and cognates thereof refers to the alkali metals selected from the group consisting of lithium, sodium, potassium, rubidium, cesium and mixtures thereof. As used herein, the term "mixtures of alkali metals" or "mixtures of higher alkali metals" or cognates of these terms refers to the use of two or more of the alkali or higher alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. A preferred alkali metal promoter is cesium. A particularly preferred alkali metal promoter is cesium plus at least one additional alkali metal. The additional alkali metal is preferably selected from sodium, lithium and mixtures thereof, with lithium being preferred.

It should be understood that the amounts of alkali metal promoters on the catalysts are not necessarily the total amounts of these metals present in the catalyst. Rather, they are the amounts of alkali metal promoters which have been added to the catalyst by impregnation with a suitable solution of ions, salts and/or compounds and/or complexes of alkali metals. These amounts do not include amounts of alkali metals which are locked into the support, for example, by calcining, or are not extractable in a suitable solvent such as water or lower alkanol or amine or mixtures thereof and do not provide a promoting effect. It is also understood that a source of the alkali metal promoter ions, salts and/or compounds used to promote the catalyst may be the carrier. That is, the carrier may contain extractable amounts of alkali metal that can be extracted with a suitable solvent, such as water or lower alkanol, thus preparing an impregnating solution from which the alkali metal ions, salts and/or compounds are deposited or redeposited on the support.

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counterions. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygen-containing compound which also may be a mixed, double or complex surface oxide. Illustrative oxidic compounds include, by way of non-limiting examples, oxides (containing only oxygen as the second element), hydroxides, nitrates, sulfates, carboxylates, carbonates, bicarbonates, oxyhalides, etc. as well as surface species wherein the element in question is bound directly or indirectly to an oxygen either in the substrate or the surface.

As used herein, the term "promoting amount" of a certain component of a catalyst refers to an amount of that component which works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced and may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operation conditions in order to take advantage of certain catalytic properties even at the expense of other catalytic properties in order to maximize profits by taking into account feedstock costs, energy costs, by-product removal costs and the like. The particular combination of silver, support, alkali metal promoter, rhenium promoter, if present, rhenium co-promoter, if present, and pre-doped rare earth and alkaline earth metal and/or Group VIII transition metal promoters of the instant invention will provide an improvement in one or more catalytic properties over the same combination of silver, support, alkali metal promoter, rhenium promoter, if present, and rhenium co-promoter, if present, and no pre-doped rare earth and alkaline earth metal and/or Group VIII transition metal promoters.

As used herein, the term "catalytically effective amount of silver" refers to an amount of silver that provides a measurable conversion of ethylene and oxygen to ethylene oxide.

In one embodiment, the pretreated or pre-doped carrier is also impregnated with rhenium ions, salt(s), compound(s), and/or complex(es). This may be done at the same time that the alkali metal promoter is added, or before or later; or at the same time that the silver is added, or before or later; or at the same time that the rhenium co-promoter, if present, is added, or before or later. Preferably, rhenium, if present, alkali metal, rhenium co-promoter, if present, and silver are in the same impregnating solution, although it is believed that their presence in different solutions will still provide suitable catalysts. When a rhenium promoter is utilized, the preferred amount of rhenium, calculated as the metal, deposited on or present on the carrier or catalyst ranges from about 0.1 micromoles per gram to about 10 micromoles per gram, more preferably from about 0.2 micromoles per gram to about 5 micromoles per gram of total catalyst, or, alternatively stated, from about 19 parts per million to about 1860 parts per million, preferably from about 37 parts per million to about 930 parts per million by weight of total catalyst. The degree of benefit obtained within the above-defined limits will vary depending upon particular properties and characteristics, such as, for example, reaction conditions, catalyst preparative conditions, surface area and pore structure and surface chemical properties of the carrier utilized, silver content of the catalyst and other compounds, anions or cations present in addition to those containing rhenium, alkali metal, or rhenium co-promoter, such as ions added with the alkali metal, rhenium or rhenium co-promoter, or compounds remaining from the impregnating technique, and the above-defined limits were selected to cover the widest possible variations in properties and characteristics. The effects of these variations are readily determined by experimentation. For purposes of convenience, the amount of rhenium present on the catalyst is expressed as the metal, irrespective of the form in which it is present.

Suitable rhenium compounds for use in the preparation of the instant catalysts are rhenium compounds that can be solubilized in an appropriate solvent. Preferably, the solvent is a water-containing solvent. More preferably, the solvent is the same solvent used to deposit the silver and the alkali metal promoter. Examples of suitable rhenium compounds include the rhenium salts such as rhenium halides, the rhenium oxyhalides, the rhenates, the perrhenates, the oxides and the acids of rhenium. A preferred compound for use in the impregnation solution is the perrhenate, preferably ammonium perrhenate. However, the alkali metal perrhenates, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, i.e., $ReO_4$. It is also understood that there are many rhenium compounds that are not soluble per se in water. However, these compounds can be solubilized by utilizing various acids, bases, peroxides, alcohols, and the like. After solubilization, these compounds could be used, for example, with an appropriate amount of water or other suitable solvent to impregnate the carriers. Of course, it is also understood that upon solubilization of many of these compounds, the original compound no longer exists after solubilization. For example, rhenium metal is not soluble in water. However, it is soluble in concentrated nitric acid as well as in hydrogen peroxide solution. Thus, by using an appropriate reactive solvent, one could use rhenium metal to prepare a solubilized rhenium-containing impregnating solution. In a preferred embodiment of the instant invention, the rhenium present on the catalyst is present in a form that is extractable in water.

U.S. Pat. No. 4,766,105, issued Aug. 23, 1988, teaches that if a rhenium co-promoter is added to an alkali metal/rhenium doped supported silver catalyst, an improvement in initial selectivity is obtained. While suitable catalysts can be prepared in the absence of both rhenium and a rhenium co-promoter, it is preferable that if the catalyst contains rhenium, the catalyst also contains a rhenium co-promoter. When a co-promoter is utilized, the co-promoter is selected from the group consisting of sulfur, molybdenum, tungsten, chromium, phosphorus, boron and mixtures thereof. The exact form of the co-promoter on the catalyst is not known. The co-promoter, it is believed, is not present on the catalyst in the elemental form since the co-promoter is applied to catalyst in the form of ions, salts, compounds and/or complexes and the reducing conditions generally used to reduce the silver to metallic silver are not usually sufficient to reduce the sulfur, molybdenum, tungsten chromium, phosphorus or boron to the elemental form. It is believed that the co-promoter deposited on the support or present on the catalyst is in the compound form, and probably in the form of an oxygen-containing or oxidic compound. In a presently preferred embodiment, the co-promoter is applied to the catalyst in the oxyanionic form, i.e., in the form of an anion, or negative ion which contains oxygen. Examples of anions of sulfur that can be suitably applied include sulfate, sulfite, bisulfite, bisulfate, sulfonate, persulfate, thiosulfate, dithionate, etc. Preferred compounds to be applied are ammonium sulfate and the alkali metal sulfates. Examples of anions of molybdenum, tungsten and chromium that can be suitably applied include molybdate, dimolybdate, paramolybdate, other iso- and hetero-polymolybdates, etc.; tungstate, paratungstate, metatungstate, other iso- and hetero-polytungstates, etc.; and chromate, dichromate, chromite, halochromate, etc. Examples of anions of phosphorus that can be suitably applied include phosphate, hydrogen phosphate, dihydrogen phosphate, metaphosphate, fluorophosphate, pyrophosphate, hypophosphate, diphosphate, triphosphate, etc. Examples of anions of boron that can suitable be applied include borate, metaborate, tetraborate, tetrafluoroborate, etc. Preferred are sulfates, molybdates, tungstates, chromates, phosphates and borates. The anions can be supplied with various counter-ions. Preferred are ammonium, alkali metal, mixed alkali metal and hydrogen (i.e. acid form). The anions can be prepared by the reactive dissolution of various non-anionic materials such as the oxides such as $SO_2$, $SO_3$, $MoO_3$, $WO_3$, $Cr_2O_3$, $P_2O_5$, $B_2O_3$, etc., as well as other materials such as halides, oxyhalides, hydroxyhalides, hydroxides, sulfides, etc., of the metals.

When a co-promoter is used, the carrier is impregnated with rhenium co-promoter ions, salt(s), compound(s) and/or complex(es). This may be done at the same time that the other components are added, or before and/or later. Preferably, rhenium co-promoter, rhenium, alkali metal and silver are in the same impregnating solution, although it is believed that their presence in different solutions will still provide suitable catalysts.

The preferred amount of co-promoter compound present on or deposited on the support or catalyst ranges from about 0.1 to about 10 micromoles, preferably from about 0.2 to about 5 micromoles, expressed as the element, per gram of total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, alkali content of the catalyst, rhenium content of the catalyst, and other compounds anions or cations present besides those containing rhenium, rhenium co-promoter and alkali metal, such as ions added with the alkali metal, rhenium or rhenium co-promoter, or compounds remaining from the impregnation technique, and the above-defined limits were selected to cover the widest possible variations in properties and characteristics. These variations are readily determined by experimentation. For purposes of convenience the amount of co-promoter present on the catalyst is expressed as the element irrespective of the form in which it is present.

The presence of the indicated and claimed promoting amount of rhenium co-promoters in this specification and claims does not preclude the use of other activators, promoters, enhancers, stabilizers, improvers, etc., and it is not intended by the use of Markush terminology in this specification and claims to exclude the use of such other activators, promoters, enhancers, stabilizers, improvers, etc.

The co-promoter compounds, salts and/or complexes suitable for use in the preparation of the instant catalysts are compounds, salts and/or complexes which can be solubilized in an appropriate solvent. Preferably, the solvent is a water-containing solvent. More preferably, the solvent is the same solvent used to deposit the silver, alkali metal promoter and rhenium. Preferred co-promoter compounds are the oxyanionic compounds of the co-promoter elements, preferably the ammonium and alkali metal oxyanionates, such as ammonium sulfate, potassium sulfate, cesium chromate, rubidium tungstate, ammonium molybdate, lithium sulfate, sodium tungstate, lithium chromate and the like.

Generally, the carrier is contacted with a rare earth salt, a rare earth compound or a rare earth complex and a alkaline earth metal and/or Group VIII transition metal salt, compound or complex which have been dissolved in aqueous or non-aqueous solutions, calcined at a temperature in the range of from about 200° C. to about 1500° C., and then contacted with a silver salt, a silver compound, or a silver complex which has been dissolved in an aqueous solution, so that the carrier is impregnated with said aqueous solution; thereafter the impregnated carrier is separated form the aqueous solution, e.g., by centrifugation or filtration and then dried. It is understood that the other dopants such as alkali metal promoter, rhenium promoter, if present, and rhenium co-promoter, if present, can be added to the silver-containing impregnation solution, if desired. The thus obtained impregnated carrier is heated to reduce the silver to metallic silver. It is conveniently heated to a temperature in the range of from about 50° C. to about 600° C., during a period sufficient to cause reduction of the silver salt, compound or complex to metallic silver and to form a layer of finely divided silver, which is bound to the surface of the carrier, both the exterior and pore surface. Air, or other oxidizing gas, reducing gas, an inert gas or mixtures thereof may be conducted over the carrier during this heating step.

The rare earth and alkaline earth metal and/or Group VIII transition metal promoters are deposited on the carrier prior to the deposition of the silver, alkali metal promoter, rhenium promoter, if present, and rhenium co-promoter, if any, and thereafter the pre-doped carrier is calcined. As used herein, the term "calcined" refers to thermal treatment at a temperature sufficient to drive off volatile liquids and to chemically bind at least a portion of the rare earth and alkaline earth metal and/or Group VIII transition metal to the support. The calcination temperatures will typically be in the range of from about 150° C. and about 1500° C., preferably between about 200° C. and about 1500° C. While not wishing to be bound by any theory, it is believed that the rare earth and the alkaline earth metal and/or Group VIII transition metal are present in an ionic form, binding to the oxygen ions present on the carrier.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 600° C. Specific solutions of silver salts with solubilizing and reducing agents may be employed as well, e.g., combinations of the vicinal alkanolamines, alkyldiamines and ammonia. One such example of a solution of silver salts comprises an impregnating solution comprising a silver salt of a carboxylic acid, an organic amine alkaline solubilizing/reducing agent, and an aqueous solvent.

One method of preparing the silver containing catalyst can be found in U.S. Pat. No. 3,702,259, issued Nov. 7, 1972, incorporated by reference herein. Other methods for preparing the silver-containing catalysts which in addition contain higher alkali metal promoters can be found in U.S. Pat. No. 4,010,115, issued Mar. 1, 1977; and U.S. Pat. No. 4,356,312, issued Oct. 26, 1982; U.S. Pat. No. 3,962,136, issued Jun. 8, 1976 and U.S. Pat. No. 4,012,425, issued Mar. 15, 1977, all incorporated by reference herein. Methods for preparing silver-containing catalysts containing higher alkali metal and rhenium promoters can be found in U.S. Pat. No. 4,761,394, issued Aug. 2, 1988, which is incorporated by reference herein, and methods for silver-containing catalysts containing higher alkali metal and rhenium promoters and a rhenium co-promoters can be found in U.S. Pat. No. 4,766,105, issued Aug. 2, 1988, which is incorporated herein be reference.

The preferred amount of alkali metal promoter deposited on or present on the surface of the carrier of catalyst generally lies between about 10 parts per million and about 3000 parts per million, preferably between about 15 parts per million and about 2000 parts per million and more preferably between about 20 parts per million and about 1500 parts per million by weight of alkali metal calculated on the total carrier material. Amounts between about 50 parts per million and about 1000 parts per million are most preferable. Suitable compounds of alkali metals comprise lithium, sodium, potassium, rubidium, cesium or mixtures thereof in a promoting amount with the even more preferred promoters being rubidium and/or cesium plus an additional alkali metal selected from lithium, sodium and mixtures thereof. Preferably the amount ranges from about 10 parts per million and about 3000 parts per million, more preferably between about 15 parts per million and about 2000 parts per million, even more preferably between about 20 parts per million and about 1500 parts per million by weight, and most preferably between about 50 parts per million and 1000 parts per million by weight. The most preferred promoter is cesium plus lithium, preferably applied in an aqueous solution having cesium nitrate or cesium hydroxide dissolved therein.

There are known excellent methods of applying the alkali metal promoter, rhenium promoter, if present, and rhenium co-promoter, if present, coincidentally with the silver on the carrier. Suitable alkali metal salts are generally those which are soluble in the silver-impregnating liquid phase. Besides the above-mentioned compounds may be mentioned the nitrites; the halides, such as fluorides, chlorides, iodides, bromides; oxyhalides; bicarbonates; borates; sulfates; sulfites; bisulfates; acetates; tartrates; lactates and isopropoxides, etc. The use of alkali metal, rhenium or co-promoter salts which have ions which react with the silver salt in solution is preferably avoided, e.g. the use of cesium chloride together with silver nitrate in an aqueous solution, since then some silver chloride is prematurely precipitated. Here the use of cesium nitrate is recommended instead of cesium chloride, for example. However, cesium chloride may be used together with a silver salt-amine-complex in aqueous solution, since then the silver chloride is not precipitated prematurely from the solution.

The alkali metal, rhenium promoters, if present, and rhenium co-promoters, if present, may be deposited on the carrier (support) or on the catalyst, depending upon the particular impregnation technique or sequence utilized. In this specification and claims, the term "on the catalyst" when referring to the deposition or presence of promoters and/or co-promoters refers to the catalyst which comprises the combination of carrier (support) and silver. Thus, the promoters, i.e., alkali metal, rhenium and rhenium co-promoter may be found individually or in a mixture thereof on the catalyst, on the support or on both the catalyst and the support. There may be, for example, alkali metal, rhenium and rhenium co-promoter on the support; alkali metal, rhenium and rhenium co-promoter on the catalyst; alkali metal, and rhenium on the support and rhenium co-promoter on the catalyst; alkali metal and rhenium co-promoter on the support and rhenium on the catalyst; alkali metal, rhenium and rhenium co-promoter on the support and rhenium and rhenium co-promoter on the catalyst and any of the other possible distributions of alkali metal, rhenium and/or rhenium co-promoter between the support and/or the catalyst.

The amount of the alkali metal, rare earth and alkaline earth metal and/or Group VIII transition metal, and/or rhenium promoters and/or rhenium co-promoters on the porous carrier or catalyst may also be regulated within certain limits by washing out the surplus of promoter material with an appropriate solvent, for example, methanol or ethanol.

A particularly preferred process of impregnating the carrier with silver, alkali metal, rhenium and rhenium co-promoter consists of impregnating the rare earth and alkaline earth metal and/or Group VIII transition metal pre-doped carrier with an aqueous solution containing a silver salt of a carboxylic acid, an organic amine, a salt of cesium, ammonium perrhenate and ammonium sulfate dissolved therein. Silver oxalate is a preferred salt. It can be prepared by reacting silver oxide (slurry in water) with (a) a mixture of ethylenediamine and oxalic acid, or (b) oxalic acid and then ethylenediamine, or (c) reacting silver oxide with an oxalic acid amine salt solution so that an aqueous solution of silver oxalate-ethylenediamine complex is obtained, to which solution is added a certain amount of cesium compound, ammonium perrhenate and ammonium sulfate. While addition of the amine to the silver oxide before adding the oxalic acid is possible, it is not preferred since it can give rise to solutions which are unstable or even explosive in nature. Other diamines and other amines, such as ethanolamine, may be added as well. A cesium-containing silver oxalate solution may also be prepared by precipitating silver oxalate from a solution of cesium oxalate and silver nitrate and rinsing with water or alcohol the obtained silver oxalate in order to remove the adhering cesium salt until the desired cesium content is obtained. The cesium-containing silver oxalate is then solubilized with ammonia and/or an amine in water and ammonium perrhenate and ammonium sulfate is added. Rubidium-, potassium-, sodium-, lithium- and mixtures of alkali metal-containing solutions may be prepared also in these ways. The impregnated carriers are then heated to a temperature between about 50° C. and about 600° C., preferably between about 75° C. and about 400° C. to evaporate the liquid and produce a metallic silver.

In general terms, the impregnation process comprises impregnating the support with one or more solutions comprising rare earth and alkaline earth metal and/or Group VIII transition metal, calcining the impregnated support, impregnating the rare earth and alkaline earth metal and/or Group VIII transition metal pre-doped support with one or more solutions comprising silver, alkali metal, and optionally, rhenium and rhenium co-promoter, and drying the support. As used in the instant specification and claims, the terminology "impregnating the support with one or more solutions comprising silver, alkali metal, rhenium and/or rhenium co-promoter", and similar or cognate terminology means that the support is impregnated in a single or multiple impregnation with one solution containing silver, alkali metal, rhenium and rhenium co-promoter in differing amounts; or in multiple impregnations with two or more solutions, wherein each solution contains at least one component selected from silver, alkali metal, rhenium and rhenium co-promoter, with the proviso that all of the components of silver, alkali metal, rhenium and rhenium co-promoter will individually be found in at least one of the solutions.

The amount of rare earth deposited, pre-impregnated or pre-doped on the support or catalyst or present on the catalyst is to be a promoting amount. Preferably, the amount of rare earth will range from about 0.05 percent by weight to about 10 percent by weight of the total catalyst, preferably from about 0.05 by weight to about 2 percent by weight of the total catalyst, expressed as the element. The upper and lower limits of preferred rare earth concentrations can be suitably varied depending upon the particular promoting effect desired or other variables involved.

The amount of alkaline earth metal and/or Group VIII transition metal deposited, pre-impregnated or pre-doped on the support or catalyst or present on the catalyst is to be a promoting amount. Preferably, the amount of alkaline earth metal and/or Group VIII transition metal will range from about 0.01 percent by weight to about 5 percent by weight of the total catalyst, preferably from about 0.02 percent by weight to about 3 percent by weight of the total catalyst, expressed as the element. The upper and lower limits of preferred alkaline earth metal and/or Group VIII transition metal concentrations can be suitably varied depending upon the particular promoting effect desired or other variables involved.

The amount of silver deposited on the support or present on the support is to be a catalytically effective amount of silver, i.e., an amount that catalyzes the reaction of ethylene and oxygen to produce ethylene oxide. Preferably this amount will range from about 1 to about 40 percent by weight of the total catalyst, more preferably from about 1 to about 25 percent by weight of the total catalyst, and even more preferably from about 5 to about 20 percent by weight of the total catalyst. The upper and lower limits of preferred silver concentrations can be suitably varied, depending upon the particular catalytic properties or effect desired or the other variables involved. The lower limit of silver is probably about 1 percent by weight of the total catalyst, and the upper limit of silver is probably about 40 percent by weight of the total catalyst.

The amount of alkali metal deposited on the support or catalyst or present on the support or catalyst is to be a promoting amount. Preferably the amount will range from about 10 parts per million to about 3000 parts per million, more preferably from about 15 parts per million to about 2000 parts per million and even more preferably from about 20 parts per million to about 1500 parts per million, and most preferably, from about 50 parts per million to about 1000 parts per million by weight of the total catalyst, expressed as the metal. The upper and lower limits of preferred alkali metal concentrations can be suitably varied depending upon the particular promoting effect desired or other variables involved. A possible lower limit of alkali metal is, for example, about 1 parts per million by weight of the total catalyst, expressed as the metal, and a possible upper limit of alkali metal is, for example, about 3000 parts per million by weight of the total catalyst, expressed as the metal.

When the catalyst contains rhenium, the amount of rhenium deposited on the support or catalyst or present on the support of catalyst is to be a promoting amount. Preferably, the amount will range from about 0.1 micromoles per gram to about 10 micromoles per gram, preferably from about 0.2 micromoles per gram to about 5 micromoles per gram, of total catalyst, expressed as the metal. The upper and lower limits of preferred rhenium concentrations can be suitably varied depending upon the particular promoting effect desired or other variables involved. A possible lower limit of rhenium is, for example, about 0.01 micromoles per gram of total catalyst, and a possible upper limit of rhenium is, for example, about 16 micromoles per gram of total catalyst, expressed as the metal.

When the catalyst contains a rhenium co-promoter, the amount of rhenium co-promoter deposited on the support or catalyst or present on the support or catalyst is to be a promoting amount. Preferably, the amount will range from about 0.1 micromoles per gram to about 10 micromoles per gram, preferably from about 0.2 micromoles per gram to about 5 micromoles per gram, of total catalyst, expressed as the element or the metal. The upper and lower limits of preferred rhenium co-promoter concentrations can be suitably varied depending upon the particular promoting effect desired or other variables involved. A possible lower limit of rhenium co-promoter is, for example, about 0.01 micromoles/gram of total catalyst, and a possible upper limit of rhenium co-promoter is, for example, about 16 micromoles/gram of total catalyst, measured as the metal.

It is observed that independent of the form in which the silver is present in the solution before precipitation on the carrier, the term "reduction to metallic silver" is used, while in the meantime often decomposition by heating occurs. We prefer to use the term "reduction", since Ag$^+$ ion is converted into a metallic Ag atom. Reduction times may generally vary from about 0.5 minute to about 8 hours, depending on the circumstances.

The silver catalysts according to the present invention have been shown to have improved selectivity stabilities for ethylene oxide production in the direct oxidation of ethylene with molecular oxygen to ethylene oxide. The conditions for carrying out such an oxidation reaction in the presence of the silver catalysts according to the present invention broadly comprise those already described in the prior art. This applies, for example, to suitable temperatures, pressures, residence times, diluent materials such as nitrogen, carbon dioxide, steam, argon, methane or other saturated hydrocarbons, to the presence of moderating agents to control the catalytic action, for example, 1-2-dichloroethane, vinyl chloride, ethyl chloride or chlorinated polyphenyl compounds, to the desirability of employing recycle operations or applying successive conversations in different reactors to increase the yields of ethylene oxide, and to any other special conditions which may be selected in processes for preparing ethylene oxide. Pressures in the range of from atmospheric to about 500 psig are generally employed. Higher pressures, however, are not excluded. Molecular oxygen employed as reactant can be obtained from conventional sources. The suitable oxygen charge may consist essentially or relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxide reactions is in no way limited to the use of specific conditions among those which are known to be effective. For purposes of illustration only, the following table shows the range of conditions that are often used in current commercial ethylene oxide reactor units.

TABLE II

| *GHSV | 1500–10,000 |
|---|---|
| Inlet Pressure | 150–400 psig |
| Inlet Feed | |
| Ethylene | 1–40% |
| O$_2$ | 3–12% |
| Ethane | 0–3% |
| Argon and/or methane and/or nitrogen diluent | Balance |
| Chlorohydrocarbon Moderator | 0.3–50 ppmv total |
| Coolant temperature | 180–315° C. |
| Catalyst temperature | 180–325° C. |
| O$_2$ conversion level | 10–60% |
| EO Production (Work Rate) | 2–25 lbs. EO/cu. ft. catalyst/hr. |

*Cubic feet of gas at standard temperature and pressure passing over one cubic foot of packed catalyst per hour.

In a preferred application of the silver catalysts according to the present invention, ethylene oxide is produced when an oxygen-containing gas is contacted with ethylene in the presence of the present catalysts at a temperature in the range of from about 180° C. to about 330° C. and preferably about 200° C. to about 325° C.

While the catalysts of the present invention are preferably used to convert ethylene and oxygen to ethylene oxide, olefins having no allylic hydrogens can be oxidized using the silver catalysts of the present invention to produce a high selectivity of epoxide derivatives thereof by contacting the olefin feed with an oxygen-containing gas in the presence of an organic halide and the silver catalyst described above under defined oxidation conditions.

The process for the selective epoxidation of olefins having no allylic hydrogens comprises contacting the feed olefin, preferably an olefin having at least 4 carbon atoms, with a sufficient quantity of an oxygen-containing gas so as to maintain the molar ratio of olefin to oxygen in the range of about 0.01 up to about 20, in the presence of an organic halide and a silver catalyst at a reaction pressure in the range of about 0.1 up to about 100 atmospheres and a temperature in the range of about 75° up to about 325° C. for a reaction time sufficient to obtain olefin conversions per pass in the range of about 0.1 up to about 75 mole percent.

Olefins contemplated for use in this oxidation process are those which satisfy the following structural formula:

wherein each R is independently selected from the group consisting of:

(a) hydrogen, (b) aryl and substituted aryl groups having in the range of 6 up to 20 carbon atoms, (c) alkyl groups of the formula:

$$R'-\underset{\underset{R'}{|}}{\overset{\overset{R'}{|}}{C}}-,$$

where each R' is independently:

$$CR_3''(CR_2'')_n-\overset{\overset{O}{\|}}{C}-, \text{ or } CR_3''(CR_2'')_n-\overset{\overset{O}{\|}}{C}-O-,$$

where R" is H, $C_1$–$C_{10}$ alkyl or substituted alkyl, an aryl or substituted aryl group having 6 up to 20 carbon atoms, and n is a whole number from 0–12;

(d) $CR_3''$—$(CR_2'')_x$—O—, where x is a whole number from 1–12;

(e)

$$R_2''N-\overset{\overset{O}{\|}}{C}-,$$

(f) $R_2''N$—;
(g) $R''S$—;
(h) $CR_2''=CR''-(CR''=CR'')_y$,
where y is an integer from 0–20; and (i)

[cyclic structure with X and $R_m''$]

where X is O, S or NR"; and m is an integer from 0–3 with the proviso that said olefin have no allylic hydrogens and that at least one R-group not be hydrogen.

Exemplary olefins which satisfy the above structural formula include butadiene, tertiary butylethylene, vinyl furan, methyl vinyl ketone, N-vinyl pyrrolidone, and the like. A presently preferred olefin for use in the practice of this process is butadiene because of its ready availability, relatively low cost, and the wide range of possible uses for the epoxide reaction product.

The epoxides produced by this process have the structural formula:

$$\underset{R}{\overset{R}{\diagdown}}C\underset{}{\overset{\overset{O}{\diagup\diagdown}}{\text{———}}}C\underset{R}{\overset{R}{\diagup}}$$

wherein each R is independently defined as set forth above. Where one or more of the R-groups contain carbon-carbon bond unsaturation, further oxidation can be carried out, thereby producing polyepoxide products.

The process is carried out by contacting the olefin to be oxidized with molecular oxygen and an organic halide under oxidation conditions, i.e. in the presence of sufficient quantities of an oxygen-containing gas to provide a molar ratio of olefin to oxygen in the range of about 0.01 up to about 20, and in the presence of about 0.1 up to about 1000 parts per million (by volume of total feed) of organic halide. Preferred quantities of organic halide for use in the practice of the present invention fall within the range of about 1 up to about 100 parts per million, by volume of total feed.

While greater or lesser quantities of molecular oxygen can be employed, sufficient quantities of oxygen should be provided to insure that undesirably low levels of olefin conversion do not occur, while excessively high oxygen concentrations should be avoided to prevent the formation of explosive mixtures. Similarly, lower levels of organic halide will provide negligible effect on catalyst performance, while higher levels of organic halide would not be expected to provide any significant improvement in catalyst performance.

Suitable oxygen-containing gases include air, oxygen enriched air, substantially purified oxygen, oxygen diluted with inert gases such as $N_2$, Ar, $CO_2$, $CH_4$ and the like.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas.

Suitable reaction temperatures fall within the range of about 75° C. up to about 325° C. At lower temperatures, the reaction proceeds so slowly as to be impractical, while at higher temperatures undesirable levels of by-products, e.g. carbon dioxide, are obtained. Preferred reaction temperatures fall within the range of about 125° C. up to about 295° C.; with temperatures in the range of about 175° C. up to about 290° C. being most preferred because selectivity to the desired epoxide falls off at temperatures significantly above about 290° C. and space-time yields are undesirably low at temperatures below about 175° C.

The reaction pressure can vary within wide ranges, with typical limits of about 0.1 up to about 100 atmospheres being chosen primarily as a function of safety, handling, equipment, and other practical considerations. Preferably, reaction pressure is maintained in the range of about 1 up to about 30 atmospheres.

Reaction times suitable for this process can vary within wide ranges. Generally, olefin, oxygen, organic halide and catalyst are maintained in contact for a time sufficient to obtain olefin conversions per pass in the range of about 0.1 up to about 75 mole percent. Preferred target olefin conversion levels per pass fall within the range of about 1 up to about 50 mole percent, while reaction times sufficient to obtain olefin conversion per pass in the range of about 5 up to about 30 mole percent are presently most preferred for efficient utilization of the reactor capacity.

Those of skill in the art recognize that the actual contact times required to accomplish the desired conversion levels can vary within wide ranges, depending on such factors as vessel size, olefin to oxygen ratios, the silver loading level on the catalyst, the presence or absence of any catalyst modifiers (and their loading levels), the amount of organic halide present in the reaction zone, the reaction temperature and pressure, and the like.

The process can be carried out in either batch or continuous mode. Continuous reaction is presently preferred since high reactor throughput and high purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 10,000 $hr^{-1}$ being most preferred because under such conditions the most desirable combination of feed olefin conversion and product selectivities are obtained.

When continuous mode of reaction is carried out in the liquid phase, typical liquid hourly space velocities (LHSV) employed will give contact times analogous to that obtained at the GHSV values given above. Most preferably, LHSV employed will fall in the range so as to produce the most desirable combination of feed olefin conversion levels and high product selectivity.

Recovery of the epoxide product produced can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like. Since the selectivity to the desired epoxide product is generally quite high, there are only small amounts of undesired reaction products from which to isolate the desired product.

Prior to use for oxidizing olefins having no allylic hydrogens, the silver catalysts (either before or after further treatment with promoter), are optionally calcined in an oxygen-containing atmosphere (air or oxygen-supplemented helium) at about 350° C. for about 4 hours. Following calcination, the silver catalysts are typically subjected to an activation treatment at a temperature in the range of about 300°–350° C. in an atmosphere initially containing about 2–5% hydrogen in an inert carrier such as helium or nitrogen. The hydrogen content of the activating atmosphere is gradually increased up to a final hydrogen concentration of about 20–25% at a controlled rate so that the activation temperature does not exceed 350° C. After the temperature is maintained for about 1 hour at a hydrogen concentration in the range of about 20–25%, catalyst is ready for use.

More detailed descriptions of the silver catalysts and their use in oxidizing olefins having no allylic hydrogens are found in U.S. Pat. Nos. 4,897,498, issued Jan. 30, 1990 and 5,081,096, issued Jan. 14, 1992, both of which are incorporated by reference herein.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The invention will be illustrated by the following illustrative embodiments which are provided for illustration only and are not intended to limit the scope of the instant invention.

ILLUSTRATIVE EMBODIMENTS

Illustrative Embodiment 1

The following illustrative embodiment describes typical preparative techniques for making the catalysts of the instant invention (and comparative catalysts) and the typical technique for measuring the properties of these catalysts.

Part A: Preparation of stock silver oxalate/ethylenediamine solution for use in catalyst preparation:

1) Dissolve 415 grams (g) of reagent-grade sodium hydroxide in 2340 milliliters (ml) deionized water. Adjust the temperature to 50° C.

2) Dissolve 1699 g of "Spectropure" (high purity) silver nitrate in 2100 ml deionized water. Adjust the temperature to 50° C.

3) Add sodium hydroxide solution slowly to silver nitrate solution with stirring while maintaining a temperature of 50° C. Stir for 15 minutes after addition is complete, and then lower the temperature to 40° C.

4) Insert clean filter wands and withdraw as much water as possible from the precipitate created in step (3) in order to remove sodium and nitrate ions. Measure the conductivity of the water removed and add back as much fresh deionized water as was removed by the filter wands. Stir for 15 minutes at 40° C. Repeat this process until the conductivity of the water removed is less than 90 μmho/cm. Then add back 1500 ml deionized water.

5) Add 630 g of high-purity oxalic acid dihydrate in approximately 100g increments. Keep the temperature at 40° C. and stir to mix thoroughly. Add the last portion of oxalic acid dihydrate slowly and monitor pH to ensure that pH does not drop below 7.8.

6) Remove as much water from the mixture as possible using clean filter wands in order to form a highly concentrated silver-containing slurry. Cool the silver oxalate slurry to 30° C.

7) Add 699 g of 92 percent weight (% w) ethylenediamine (8% deionized water). Do not allow the temperature to exceed 30° C. during addition.

The above procedure yields a solution containing approximately 27–33% w silver.

Part B: Catalyst pre-doping procedure

For Catalyst A, in order to deposit 0.54 percent by weight, basis the total weight of the carrier, of lanthanum ions, and 0.23 percent by weight, basis the total weight of carrier, of cobalt ions, the following solution is made. 150 Grams of water was acidified with 9.5 grams of acetic acid. 5.0 Grams of $Co(CH_3COO)_2 4H_2O$ and 8.69 grams of $La(NO_3)_3 6H_2O$ were dissolved with stirring, followed by 9.0 grams of monoethanolamine. The volume of the solution thus prepared was adjusted to a total volume of 200 milliliters. Two hundred (200) grams of Catalyst carrier C which is described in Table 1 is then vacuum impregnated at 25–50 millimeters (mm) vacuum for three minutes. At the end of this time, the vacuum is released and the excess solution is decarrier is the carrier. The carrier is then dried by continuous shaking in a 300 cu. ft./hr. air stream at 270° C. for ten minutes. This drying step is followed by calcination in air; two hours at a temperature of 500° C. followed by four hours at a temperature of 1050° C.

For Catalyst B, in order to deposit 0.27 percent by weight, basis the total weight of the carrier, of cerium ions, and 0.047 percent by weight, basis the total weight of carrier, of magnesium ions, the following solution is made. 2.56 Grams of $Mg(NO_3)_2.6H_2O$, 5.48 grams of $(NH_4)Ce(NO_3)_6$ and 10.5 grams of acetic acid were dissolved in 150 milliliters of water, followed by the addition of 10.0 grams of monoethanolamine. The volume of the solution thus prepared was adjusted to a total volume of 200 milliliters. Two hundred and fifty (250) grams of Catalyst carrier C which is described in Table 1 is then vacuum impregnated at 25–50 millimeters (mm) vacuum for three minutes. At the end of this time, the vacuum is released and the excess solution is decanted from the carrier. The carrier is then dried by continuous shaking in a 300 cu. ft./hr. air stream at 270° C. for twenty minutes. This drying step is followed by calcination in air; two hours at a temperature of 500° C. followed by four hours at a temperature of 1050° C.

For Catalyst C, in order to deposit 0.583 percent by weight, basis the total weight of the carrier, of neodymium ions, and 0.24 percent by weight, basis the total weight of carrier, of cobalt ions, the following solution is made. 7.5 Grams of $Co(CH_3COO)_2.4H_2O$ and 10.18 grams of Nd(CH$_3$COO).H$_2$O were dissolved in 250 milliliters of water, followed by the addition of 14.25 grams of acetic acid and 13.5 grams of monoethanolamine. The volume of the solution thus prepared was adjusted to a total volume of 300 milliliters. Four hundred (400) grams of Catalyst carrier C which is described in Table 1 is then vacuum impregnated at 25–50 millimeters (mm) vacuum for three minutes. At the end of this time, the vacuum is released and the excess solution is decanted from the carrier. The carrier is then dried by continuous shaking in a 300 cu. ft./hr. air stream at 270° C. for ten minutes. This drying step is followed by calcination in air; two hours at a temperature of 500° C. followed by four hours at a temperature of 1050° C.

For Catalyst D, no pre-doping of Catalyst carrier C was carried out.

Part C: Preparation of impregnated catalysts

Catalyst A (Pre-doped with lanthanum and cobalt)

For preparing impregnated Catalyst A, into a 10 ml beaker is added 0.124 g of NH$_4$ReO$_4$ and approximately 3 g of deionized water, and the mixture is allowed to dissolve with stirring. 0.059 g of Li$_2$SO$_4$.H$_2$O is dissolved in 1 ml of water in a weighing dish, and then added to the perrhenate solution. 0.255 g of LiNO$_3$ is dissolved in 2 ml of water and added to the perrhenate solution. The perrhenate/lithium sulfate/lithium nitrate solution is allowed to stir, ensuring complete dissolution. This dopant solution is then added to 137 g of the above-prepared silver solution (specific gravity=1.575 g/cc), and the resulting solution is diluted with water to a total weight of 153 g. One-third of this solution is used to prepare a catalyst. 0.0998 g of stock CsOH solution containing 45.5 percent weight cesium is added to a 51 g portion of the silver oxalate/dopant solution to prepare the final impregnation solution.

The final impregnation solution thus prepared is then used to impregnate a cesium pre-doped carrier in the manner described below.

Approximately 30 g of the cesium pre-doped carrier described above for Catalyst A are placed under 25mm vacuum for 3 minutes at room temperature. Approximately 50 g of doped impregnating solution is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. The impregnated carrier is then cured by being continuously shaken in a 300 cu. ft/hr. air stream flowing across a cross-sectional area of approximately 3–5 square inches at 250°–270° C. for 5–6 minutes. The cured lanthanum and cobalt pre-doped catalyst (Catalyst A) is then ready for testing.

Catalyst B (Pre-doped cerium and magnesium)

Catalyst B was prepared in the same manner as Catalyst A, except that the catalyst carrier was pre-doped with cerium and magnesium instead of lanthanum and cobalt, and the amount of cesium was adjusted to 0.1116 grams of 45.5% cesium hydroxide solution.

Catalyst C (Pre-doped neodymium and cobalt)

Catalyst C was prepared in the same manner as Catalyst A, except that the catalyst carrier was pre-doped with neodymium and cobalt instead of lanthanum and cobalt, and the amount of cesium was adjusted to 0.1265 grams of 45.5% cesium hydroxide solution.

Catalyst D (No pre-dopants)

Catalyst D was prepared in the same manner as Catalyst A, except that the catalyst carrier was not pre-doped, and the amount of cesium was adjusted to 0.0952 grams of 45.5% cesium hydroxide solution.

The procedures set forth above for Catalysts A, B, C and D will yield catalysts on this carrier which contain approximately 13.2% w–14.5% w Ag with the following approximate dopant levels (expressed in parts per million by weight basis the weight of the total catalyst, i.e., ppmw, and percent by weight basis the weight of the total catalyst, i.e., % wt.) and which are approximately optimum in cesium for the given silver and rhenium, if present, and sulfur levels and support with regard to initial selectivity under the test conditions described below.

| | Rare Earth Pre-Dopant, % wt. | Group VII Pre-Dopant, % wt. | Cs, ppmw | Re, ppmw | S, ppmw |
|---|---|---|---|---|---|
| Catalyst A | 0.54 (La) | 0.23 (Co) | 470 | 280 | 48 |
| Catalyst B | 0.27 (Ce) | 0.047 (Mg) | 504 | 280 | 48 |
| Catalyst C | 0.583 (Nd) | 0.24 (Co) | 448 | 280 | 48 |
| Catalyst D | None | None | 430 | 280 | 48 |

The actual silver content of the catalyst can be determined by any of a number of standard, published procedures. The actual level of rhenium on the catalysts prepared by the above process can be determined by extraction with water, followed by spectrophotometric determination of the rhenium in the extract. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Perkin Elmer Model 1100 B or equivalent). It should be noted that the cesium content of the catalyst as determined by the water leaching technique may be lower than the cesium content of the catalyst as determined by the radiotracer technique.

Part D: Standard Microreactor Catalyst Test Conditions/Procedure

For Catalysts A, B, C and D 3 to 5 grams of crushed catalyst (14–20 mesh) are loaded into a ¼ inch diameter stainless steel U-shaped tube. The U tube is immersed in a molten metal bath (heat medium) and the ends are connected to a gas flow system. The weight of the catalyst used and the inlet gas flow rate are adjusted to achieve a gas hourly space velocity of 3300 cc of gas per cc of catalyst per hour. The inlet gas pressure is 210 psig.

The gas mixture passed thorough the catalyst bed (in once-through operation) during the entire test run (including startup) consists of 30% ethylene, 8.5% oxygen, 5% carbon dioxide, 54.5% nitrogen, and 2.0 to 6.0 ppmv ethyl chloride.

The initial reactor (heat medium) temperature is 225° C. The temperature is ramped at a rate of 10° C. per hour from 225° C. to 245° C., and then adjusted so as to achieve a constant oxygen conversion level of 40%. Performance data at this conversion level are usually obtained when the catalyst has been on stream for a total of at least 1–2 days. Due to slight differences in feed gas composition, gas flow rates, and the calibration of analytical instruments used to determine the feed and product gas compositions, the measured selectivity and activity of a given catalyst may vary slightly from one test run to the next. To allow meaningful comparison of the performance of catalysts tested at different times, all catalysts described in this illustrative embodiment were tested simultaneously with a reference catalyst. All performance data reported in this illustrative embodiment are corrected relative to the average initial performance of the reference catalyst ($S_{40}$=81.0%; $T_{40}$=230° C.).

After obtaining initial performance values for selectivity at 40% conversion the catalysts are subjected to accelerated aging conditions. The oxygen conversion is brought to 85% or 285° C., whichever first occurs. Once the temperature reaches 285° C., there is no further increase in temperature and the catalyst is aged at 285° C. Every ten days, the temperature is lowered and the data for 40% oxygen conversion is collected. The results can be seen in FIG. 1.

Detailed Description of the Drawing

Figure 1:
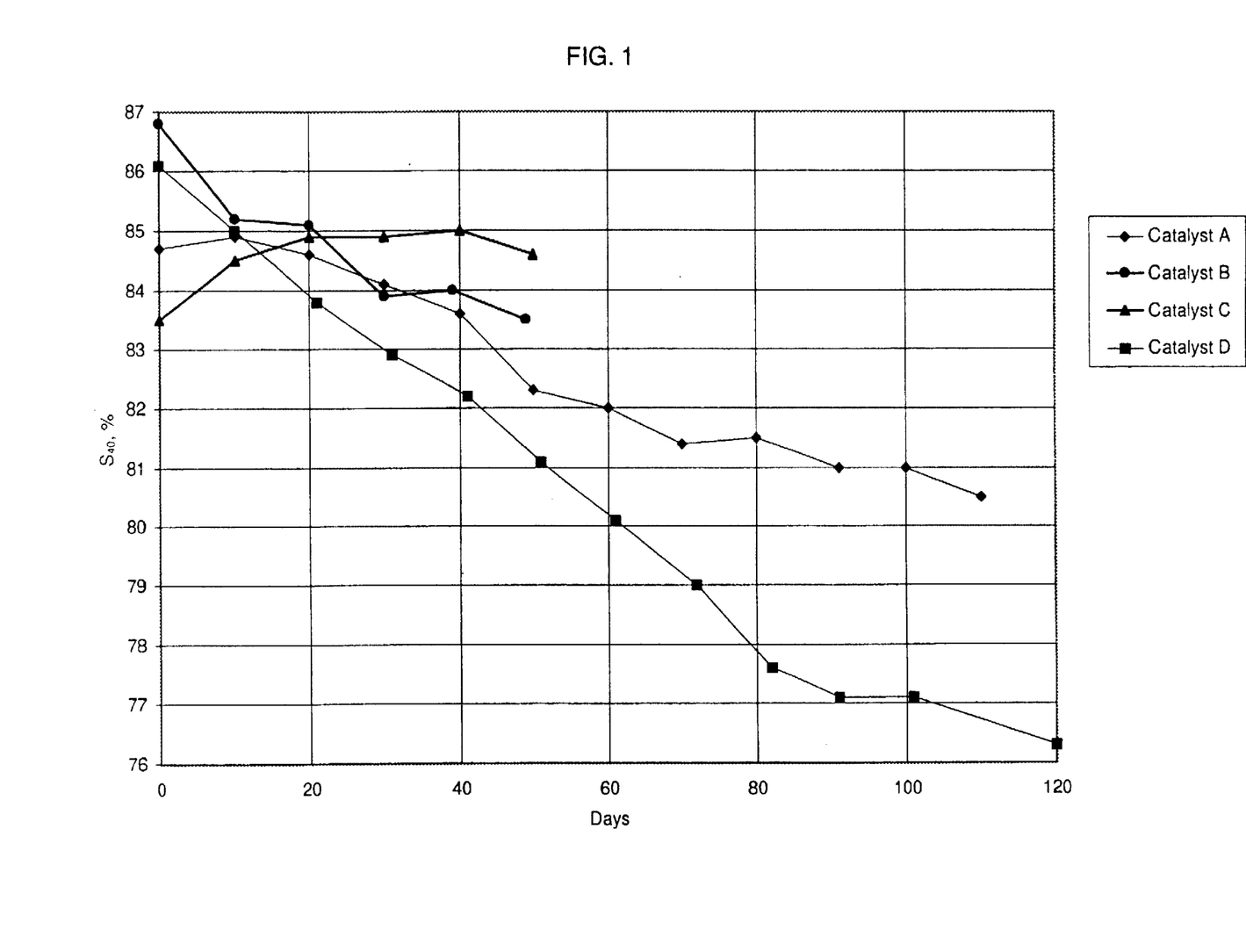
FIG. 1 shows the selectivity decline in accelerated decline testing for Catalysts A (carrier pre-doped with lanthanum and cobalt), B (carrier pre-doped with cerium and magnesium), C (carrier pre-doped with neodymium and cobalt) and D (carrier not pre-doped) at 40 mole percent oxygen conversion, ($S_{40}$), over a time period expressed in days.

As mentioned previously, selectivity decline is of tremendous economic importance when choosing a catalyst, and retarding this decline rate can lead to significant savings in costs. As can be seen in FIG. 1, catalysts which are prepared using a pre-doped rare earth and Group VIII transition metal carrier, Catalysts A and C, and using a pre-doped rare earth and alkaline earth metal carrier, Catalyst B, decline less rapidly than catalysts prepared without using a pre-doped rare earth and a Group VIII transition metal carrier, Catalyst D, and are thus significantly advantaged.

What is claimed is:

1. A process for preparing a catalyst suitable for the vapor phase production of ethylene oxide from ethylene and oxygen which process comprises depositing a promoting amount of a salt of a rare earth metal and a promoting amount of a salt of a metal selected from the group consisting of an alkaline earth metal, a Group VIII transition metal and mixtures thereof, on a support having a surface area in the range of from about 0.05 m²/g to about 10 m²/g, calcining the support, and thereafter depositing a catalytically effective amount of silver and a promoting amount of alkali metal on said support, and thereafter drying the support.

2. The process of claim 1 wherein the rare earth metal is selected from the group consisting of lanthanum, cerium, neodymium, samarium, gadolinium, dysprosium, erbium, ytterbium, and mixtures thereof.

3. The process of claim 1 wherein the alkaline earth metal is selected from the group consisting of magnesium, calcium, strontium, barium, and mixtures thereof.

4. The process of claim 1 wherein the Group VIII transition metal is selected from the group consisting of cobalt, iron, nickel, ruthenium, rhodium, palladium and mixtures thereof.

5. The process of claim 1 wherein the support comprises a porous refractory oxide.

6. The process of claim 5 wherein the support comprises alpha alumina.

7. The process of claim 6 wherein the support surface area is in the range of from about 0.05 m²/g to about 5 m²/g.

8. The process of claim 1 wherein the alkali metal is selected from potassium, rubidium, cesium, and mixtures thereof.

9. The process of claim 8 wherein the alkali metal is potassium.

10. The process of claim 8 wherein the alkali metal is rubidium.

11. The process of claim 8 wherein the alkali metal is cesium.

12. The process of claim 8 wherein the alkali metal comprises cesium plus at least one additional alkali metal.

13. The process of claim 12 wherein the alkali metal is cesium plus potassium.

14. The process of claim 12 wherein the alkali metal is cesium plus rubidium.

15. The process of claim 12 wherein the alkali metal is cesium plus lithium.

16. The process of claim 1 wherein the amount of rare earth metal promoter is in the range of from about 0.05 percent by weight to about 10 percent by weight of the total catalyst, expressed as the element, the amount of alkaline earth metal promoter and/or Group VII transition metal promoter is in the range of from about 0.01 percent by weight to about 5 percent by weight of the total catalyst, expressed as the element, the amount of silver is in the range of from about 1 percent by weight to about 40 percent by weight of the total catalyst, and the amount of alkali metal promoter is in the range of from about 10 parts per million to about 1500 parts per million, expressed as the metal, by weight of the total catalyst.

17. A process for preparing a catalyst suitable for the vapor phase production of ethylene oxide from ethylene and oxygen which process comprises depositing a promoting amount of a salt of a rare earth metal and a promoting amount of a salt of a metal selected from the group consisting of an alkaline earth metal, a Group VIII transition metal and mixtures thereof, on a support having a surface area in the range of from about 0.05 m²/g to about 10 m²/g, calcining the support, and thereafter depositing a catalytically effective amount of silver, a promoting amount of alkali metal and a promoting amount of rhenium on said support, and thereafter drying the support.

18. The process of claim 17 wherein the rare earth metal is selected from the group consisting of lanthanum, cerium, neodymium, samarium, gadolinium, dysprosium, erbium, ytterbium, and mixtures thereof.

19. The process of claim 17 wherein the alkaline earth metal is selected from the group consisting of magnesium, calcium, strontium, barium, and mixtures thereof.

20. The process of claim 17 wherein the Group VIII transition metal is selected from the group consisting of cobalt, iron, nickel, ruthenium, rhodium, palladium, and mixtures thereof.

21. The process of claim 17 wherein the support comprises a porous refractory oxide.

22. The process of claim 21 wherein the support comprises alpha alumina.

23. The process of claim 22 wherein the support surface area is in the range of from about 0.05 m²/g to about 5 m²/g.

24. The process of claim 17 wherein the alkali metal is selected from potassium, rubidium, cesium, and mixtures thereof.

25. The process of claim 24 wherein the alkali metal is potassium.

26. The process of claim 24 wherein the alkali metal is rubidium.

27. The process of claim 24 wherein the alkali metal is cesium.

28. The process of claim 24 wherein the alkali metal comprises cesium plus at least one additional alkali metal.

29. The process of claim 28 wherein the alkali metal is cesium plus potassium.

30. The process of claim 28 wherein the alkali metal is cesium plus rubidium.

31. The process of claim 28 wherein the alkali metal is cesium plus lithium.

32. The process of claim 17 wherein the rhenium is applied to the support in the form of a perrhenate or rhenium heptoxide.

33. The process of claim 17 wherein the alkali metal and rhenium are found individually or in any mixture thereof on the catalyst, on the support or on both the catalyst and the support.

34. The process of claim 17 wherein the promoting amount of a salt of a rare earth metal is in the range of from about 0.05 percent by weight to about 10 percent by weight of the total catalyst, expressed as the element, the promoting amount of a salt of a metal selected from the group consisting of an alkaline earth metal, a Group VIII transition metal and mixtures thereof, is in the range of from about 0.01 percent by weight to about 5 percent by weight of the total catalyst, expressed as the element, the amount of silver is in the range of from about 1 percent by weight to about 40 percent by weight of the total catalyst, the amount of alkali metal promoter is in the range of from about 10 parts per million to about 1500 parts per million, expressed as the metal, by weight of the total catalyst, and the amount of rhenium promoter is in the range of from about 0.1 micromoles to about 10 micromoles of rhenium, expressed as the metal, per gram of total catalyst.

35. A process for preparing a catalyst suitable for the vapor phase production of ethylene oxide from ethylene and oxygen which process comprises depositing a promoting amount of a salt of a rare earth metal and a promoting amount of a salt of a metal selected from the group consisting of an alkaline earth metal, a Group VIII transition metal and mixtures thereof, on a support having a surface area in the range of from about 0.05 $m^2$/g to about 10 $m^2$/g, calcining the support, and thereafter depositing a catalytically effective amount of silver, a promoting amount of alkali metal, a promoting amount of rhenium and a rhenium co-promoter on said support, and thereafter drying the support.

36. The process of claim 35 wherein the rare earth metal is selected from the group consisting of lanthanum, cerium, neodymium, samarium, gadolinium, dysprosium, erbium, ytterbium, and mixtures thereof.

37. The process of claim 35 wherein the alkaline earth metal is selected from the group consisting of magnesium, calcium, strontium, barium, and mixtures thereof.

38. The process of claim 35 wherein the Group VIII transition metal is selected from the group consisting of cobalt, iron, nickel, ruthenium, rhodium, palladium, and mixtures thereof.

39. The process of claim 35 wherein the support comprises a porous refractory oxide.

40. The process of claim 39 wherein the support comprises alpha alumina.

41. The process of claim 40 wherein the support surface area is in the range of from about 0.05 $m^2$/g to about 5 $m^2$/g.

42. The process of claim 35 wherein the alkali metal is selected from potassium, rubidium, cesium, and mixtures thereof.

43. The process of claim 42 wherein the alkali metal is potassium.

44. The process of claim 42 wherein the alkali metal is rubidium.

45. The process of claim 42 wherein the alkali metal is cesium.

46. The process of claim 42 wherein the alkali metal comprises cesium plus at least one additional alkali metal.

47. The process of claim 46 wherein the alkali metal is cesium plus potassium.

48. The process of claim 46 wherein the alkali metal is cesium plus rubidium.

49. The process of claim 46 wherein the alkali metal is cesium plus lithium.

50. The process of claim 35 wherein the rhenium co-promoter comprises an oxidic compound or an oxyanion.

51. The process of claim 35 wherein the rhenium co-promoter is selected from sulfate, sulfite, sulfonate, molybdate, tungstate, chromate, borate, phosphate and mixtures thereof.

52. The process of claim 35 wherein the promoting amount of a salt of a rare earth metal is in the range of from about 0.05 percent by weight to about 10 percent by weight of the total catalyst, expressed as the element, the promoting amount of a salt of a metal selected from the group consisting of an alkaline earth metal, a Group VIII transition metal and mixtures thereof, is in the range of from about 0.01 percent by weight to about 5 percent by weight of the total catalyst, expressed as the element, the amount of silver is in the range of from about 1 percent by weight to about 40 percent by weight of the total catalyst, the amount of alkali metal promoter is in the range of from about 10 parts per million to about 1500 parts per million, expressed as the metal, by weight of the total catalyst, the amount of rhenium promoter is in the range of from about 0.1 micromoles to about 10 micromoles of rhenium, expressed as the metal, per gram of total catalyst, and the amount of rhenium co-promoter is in the range of from about 0.1 micromoles to about 10 micromoles of co-promoter, expressed as the element, per gram of total catalyst.

* * * * *